United States Patent
Liu et al.

(10) Patent No.: US 6,597,937 B2
(45) Date of Patent: Jul. 22, 2003

(54) SELF-ADAPTIVE TRACKING AND PHASE ENCODING DURING DATA COLLECTION FOR CONTRAST-ENHANCED MRA AND DYNAMIC AGENT UPTAKE STUDIES

(75) Inventors: Kecheng Liu, Solon, OH (US); Jasjit S. Suri, Mayfield Heights, OH (US); Thomas S. Cull, Willoughby Hills, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 169 days.

(21) Appl. No.: 09/776,964

(22) Filed: Feb. 5, 2001

(65) Prior Publication Data

US 2002/0107438 A1 Aug. 8, 2002

(51) Int. Cl.$^7$ .............................. A61B 5/055; A61B 5/05
(52) U.S. Cl. ...................... 600/420; 600/410; 324/306; 324/309
(58) Field of Search ................................ 600/420, 410, 600/407, 419, 425, 416–418; 382/128–132; 128/916–923; 324/306, 307

(56) References Cited

U.S. PATENT DOCUMENTS

| | | | |
|---|---|---|---|
| 6,067,465 A | 5/2000 | Foo et al. | 600/410 |
| 6,167,293 A | 12/2000 | Chenevert | 600/420 |
| 6,195,579 B1 * | 2/2001 | Carroll et al. | 600/420 |
| 6,408,201 B1 * | 6/2002 | Foo et al. | 600/410 |
| 6,415,171 B1 * | 7/2002 | Gueziec et al. | 600/407 |

FOREIGN PATENT DOCUMENTS

WO    WO 97/24064    7/1997

OTHER PUBLICATIONS

Carroll, T. J. et al., "Method for Rapidly Determining and Reconstructing the Peak Arterial Frame From a Time–Resolved CE–MRA Exam", *Magnetic Resonance in Medicine*, Nov. 2000, Wiley, USA, vol. 44, No. 5, pp. 817–820, XP002212883.

Foo, T. K. F. et al., "Automated Detection of Bolus Arrival and Initiation of Data Acquisition in Fast, Three–dimensional, Gadolinium–enhanced MR Angiography", *Radiology*, Oak Brook, Il., US, vol. 203, No. 1, Apr. 1, 1997, pp. 275–280, XP002037188.

Mistretta, C. A. et al., "3D Time–Resolved Contrast–Enhanced MR DSA: Advantages and Tradeoffs", *Magnetic Resonance in Medicine*, Oct. 1998, Williams & Wilkins, USA, vol. 40, No. 4, pp. 571–581, XP02212794.

(List continued on next page.)

Primary Examiner—Mark Paschall
(74) Attorney, Agent, or Firm—Fay, Sharpe, Fagan, Minnich & McKee, LLP (57) ABSTRACT

A magnetic resonance imaging method includes acquiring a baseline magnetic resonance image of a region of interest in the absence of a contrast agent and simulating an increase in image intensity of a subregion of interest within the region of interest which is subject to increased image intensity in the presence of a contrast agent. The magnetic resonance k-space signal intensity is correlated with contrast agent concentration in the subregion and a contrast agent is administered to the subject. As k-space data for the region of interest is acquired, the signal intensity is monitored to derive contrast agent concentration information. When the peak contrast agent concentration is detected from the monitored k-space data signal intensity, the phase encoding is adjusted so that k-space data with zero phase encoding is acquired. In a further aspect, a magnetic resonance imaging apparatus is also provided.

24 Claims, 4 Drawing Sheets

OTHER PUBLICATIONS

Strecker, R., et al., "Fast Functional MRA Using Time-Resolved Projection MR Angiography With Correlation Analysis", *Magnetic Resonance in Medicine,* Feb. 2000, Wiley, USA, vol. 43, No. 2, pp. 303–309, XP002212795.

Foo, et al., "Automated Detection of Bolus Arrival and Initiation of Data Acquisition in Fast, Three–dimensional, Gadolinium–enhanced MR Angiography", Magnetic Resonance in Medicine, V. 30, No. 6, Dec. 1993 Radiology 1997; 203:275–280.

Chenevert, et al. "Dynamic Three–dimensional Imaging with Partial K–Space Sampling: Initial Application for Gadolinium–enhanced Rate Characterization of Brest Lesions", Radiology 1995; 196:135–142.

Taylor, et al. "A Rapid Interleaved Method for Measuring Signal Intensity Curves in Both Blood and Tissue During Contrast Agent Administration", MRM 30:744–749 (1993).

Wilman, et al. "Improved Centric Phase Encoding Orders for Three–Dimensional Magnetization–Prepared MR Angiography", MRM 36:384–392 (1996).

Wilman, et al. "Performance of an Elliptical Centric View Order for Signal Enhancement and Motion Artifact Suppression in Breath–hold Three–Dimensional Gradient Echo Imaging", MRM 38:793–802 (1997).

Prince, et al. "Contrast–enhanced Abdominal MR Angiography: Optimization of Imaging Delay Time by Automating the Detection of Contrast Material Arrival in the Aorta", Radiology 1997; 203:109–114.

Wilman, et al. "Fluoroscopically Triggered Contrast–enhanced Three–dimensional MR Angiography with Elliptical Centric View Order: Application to the Renal Arteries", Radiology 1997; 205:137–146.

Korosec, et al. "Time–Resolved Contrast–Enhanced 3D MR Angiography", MRM 36:345–351 (1996).

Mistretta, et al. "3D Time–Resolved Contrast–Enhanced MR DSA: Advantages and Tradeoffs", MRM 40:571–581 (1998).

\* cited by examiner

SELF-ADAPTIVE TRACKING AND PHASE ENCODING DURING DATA COLLECTION FOR CONTRAST-ENHANCED MRA AND DYNAMIC AGENT UPTAKE STUDIES

BACKGROUND OF THE INVENTION

The present invention relates generally to the art of diagnostic imaging. It finds particular application to contrast-enhanced magnetic resonance angiography (MRA) and dynamic agent uptake studies. Although the present invention is illustrated and described herein primarily with reference to magnetic resonance angiography, it will be appreciated that the present invention is also amenable to other magnetic resonance imaging techniques and to subjects other than the human body.

Commonly, in MRI, a substantially uniform temporally constant main magnetic field ($B_0$) is set up in an examination region in which a subject being imaged or examined is placed. Via magnetic resonance radio frequency (RF) excitation and manipulations, selected magnetic dipoles in the subject which are otherwise aligned with the main magnetic field are tipped to excite magnetic resonance. The resonance is typically manipulated to induce detectable magnetic resonance echoes from a selected region of the subject. In imaging, the echoes are spatially encoded via magnetic gradients set up in the main magnetic field. The raw data from the MRI scanner is collected into a matrix, commonly known as k-space. By employing inverse Fourier, two-dimensional Fourier, three-dimensional Fourier, or other known transformations, an image representation of the subject is reconstructed from the k-space data.

Because the vascular system contains flowing blood, a moving entity, a number of magnetic resonance angiography (MRA) techniques have been developed for imaging the vascular system. Time-of-flight (TOF) techniques rely on the time interval between the transverse excitation of spins and the acquisition of the resulting magnetic resonance signal to distinguish between moving and stationary spins. During the time interval, fresh spins move into the region from which the magnetic resonance signal is acquired and excited spins move out of the region. In contrast, the stationary spins remain fixed during the interval between RF excitation and data acquisition, with the result that the magnetic resonance signal produced by stationary spins is substantially different in magnitude from that produced by moving spins. When an image is reconstructed from such magnetic resonance signals, the image pixels which correspond to moving spins are either much brighter or much darker than image pixels corresponding to stationary spins, depending on the sequence. In this manner, the vascular system that transports moving blood is made to appear brighter or darker than the surrounding stationary or slowly moving tissues in the resultant image.

Phase contrast (PC) techniques rely on the fact that the phase of the magnetic resonance signal produced by moving spins is different from the phase of magnetic resonance signals produced by stationary or slowly moving spins. Phase contrast methods employ magnetic field gradients during the magnetic resonance pulse sequence which cause the phase of the resulting magnetic resonance signals to be modulated as a function of spin velocity. The phase of the magnetic resonance signals can, therefore, be used to control the contrast, or brightness, of the pixels in the reconstructed image. Since blood moves relatively fast, the vascular system is made to appear brighter or darker in the resulting image.

Because the above-described TOF and PC techniques are subject to drawbacks or shortcomings, contrast-enhanced MRA techniques have been developed to enhance the diagnostic capability of MRA. In contrast-enhanced MRA, a contrast agent such as gadolinium is injected into the patient prior to the scan. Typically, the injection is carefully timed so that the central lines of k-space, which govern image contrast resolution, are acquired during peak arterial enhancement, i.e., when the contrast agent concentration reaches a peak or plateau in the vasculature of interest. Similarly, in a dynamic uptake study, an agent which targets one or more specific organs or tissues of the body is administered to the patient and region of interest is imaged in an magnetic resonance scanner to gauge the rate at which the agent is taken into the organ or tissue of interest.

Currently, two methods are widely used for timing the data acquisition to coincide with bolus arrival in MRA, namely, central phase encoding and time-resolved imaging of contrast kinetics (TRICKS). The centric phase encoding method collects the most important low-frequency encoded data at the projected center of the plateau. The TRICKS method samples the central region of k-space more frequently than the other regions of k-space to increase the odds that the centrally phase encoded data will be generated with the plateau.

Figure 1A:
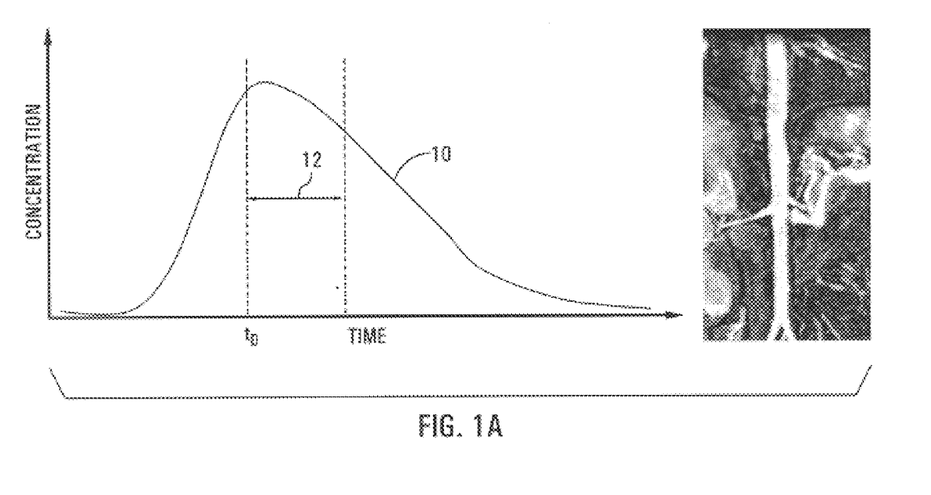
FIGS. 1A and 1B are graphs of bolus concentration vs. time.
Figure 1B:
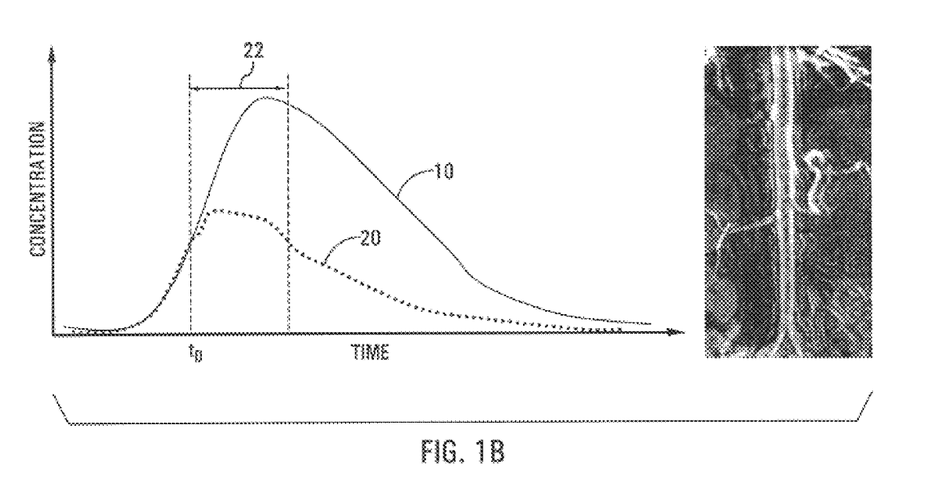

The major drawback of the central phase encoding method is that it is based on assumed arrival characteristics of the bolus, i.e., the "best guess" of bolus arrival. The success of centric phase encoding also depends on the reliability of bolus detection, i.e., at which phase it is triggered. FIG. 1A is a graph of bolus concentration in the region of interest as a function of time, and shows the correct bolus detection time $t_D$ resulting in a central phase encoding data collection window 12 which captures the peak or plateau period of the concentration curve 10. However, if the assumed arrival characteristics differ from the real curve 10 such that the detected time point $t_D$ is not sufficiently close to the plateau period, significant image artifacts may result or, in the worst case, the images may be clinically useless. FIG. 1B shows the effect of such a disparity between the real curve 10 and an assumed curve 20. In the example shown, the assumed curve 20 results in an early detection time $t_D$, resulting in centric phase encoding 22 which does not capture the plateau period.

Figure 2A:
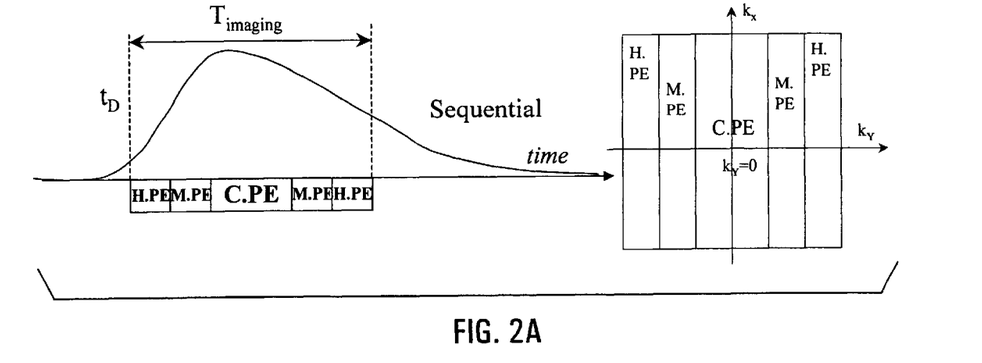
FIG. 2A illustrates an idealized sequential acquisition employing segmentation of k-space for optimal contrast and spatial resolution.

The TRICKS method does not rely on assumed arrival characteristics of the bolus. By sampling the center of k-space at a higher frequency, the probability of catching the plateau period increases. However, this method can be understood as "blind" oversampling of the center of k-space and thus, lacks assured accuracy. No timing for triggering the acquisition is necessary for TRICKS, and the success of this method depends mainly on the arrangement or strategy of phase encoding sequences (different weighting factors for k-space) and whether the plateau period is actually captured during a central phase encoding segment. One drawback of TRICKS is that while the central (contrast governing) portion of k-space is sampled more, the other (spatial resolution governing) portions of k-space are sampled less, thus resulting in a loss of high and middle frequency spatial information and potentially causing blurring of the image. FIG. 2A illustrates an idealized k-space segmentation strategy wherein the high contrast resolution (C.PE) data lines are centrally located in k-space and the high frequency data lines (H.PE) are located at the periphery of k-space. In FIG. 2A, each segment H.PE (high frequency phase encoding), M.PE (middle frequency phase encoding), and C.PE (centric or low frequency phase encoding) is sampled only once during a time window of $T_{imaging}$.

Figure 2B:
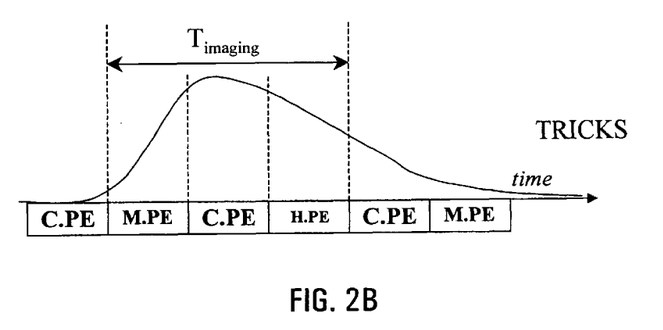
FIGS. 2B and 2C illustrated successful and unsuccessful TRICKS implementations, respectively.
Figure 2C:
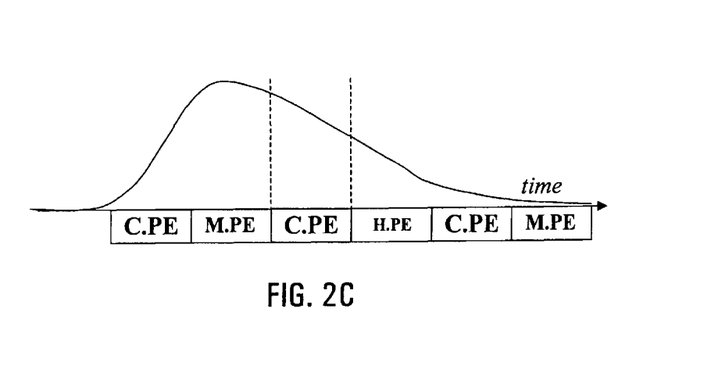

In the TRICKS implementations of FIGS. 2B and 2C, the low frequency central segment (C.PE) is sampled more than the other segments. While, this increases the likelihood capturing the plateau during central phase encoding, it does not necessarily do so. FIG. 2B shown an ideal TRICKS implementation wherein one of the C.PE segments has successfully captured the plateau period. In the TRICKS implementation of FIG. 2C, however, no C.PE segment captures the plateau ideally.

Accordingly, the present invention contemplates a new and improved contrast-enhanced MRA apparatus and method wherein phase encoding steps are dynamically adjusted according to time varying information and which overcomes the above-referenced problems and others.

SUMMARY OF THE INVENTION

In accordance with a first aspect of the present invention, a method of magnetic resonance imaging includes acquiring a baseline magnetic resonance image of a region of interest in the absence of a contrast agent and simulating an increase in image intensity of a subregion of interest within the region of interest which is subject to increased image intensity in the presence of a contrast agent. The magnetic resonance k-space signal intensity is correlated with contrast agent concentration in the subregion and a contrast agent is administered to the subject. As k-space data for the region of interest is acquired, the signal intensity is monitored to derive contrast agent concentration information. When the peak contrast agent concentration is detected from the monitored k-space data signal intensity, the phase encoding is adjusted so that low frequency part of k-space data with zero phase encoding is acquired.

In accordance with another aspect, a magnetic resonance imaging system includes means for generating a magnetic field in an examination region, a radio frequency pulse controller and transmitter for inducing dipoles in the examination region to resonance such that radio frequency resonance signals are generated, gradient magnetic field coils and a gradient magnetic field controller for performing a pulse sequence including at least phase and read magnetic field gradient pulses in orthogonal directions across the examination region, a receiver for receiving and demodulating the radio frequency magnetic resonance signals, and an image processing system for reconstructing image representations. The image processing system includes a memory for storing a baseline image representation of a region of interest in the absence of a contrast agent and a first processor for identifying the spatial location of a subregion of interest within the region of interest and for generating and storing simulated image representations of the region of interest in which the signal intensity is numerically simulated. A second image processor calculates and stores frequency domain spectra for the subregion of interest based on differences between the baseline image and the simulated images and a third processor that detects peak contrast agent concentration in the region of interest by monitoring k-space signal intensity received after a contrast agent is administered to a subject to be imaged. The gradient magnetic field controller responds to detection of the peak contrast agent composition by dynamically adjusting the pulse sequence to collect k-space data lines with central phase encoding, and a reconstruction processor generates image representations from the magnetic resonance signals.

In accordance with yet another aspect of the present invention, a method of magnetic resonance imaging includes generating a plurality of data lines high and middle frequency phase encoding and comparing a frequency spectrum of each data line with a reference frequency spectrum indicative of a presence of contrast agent peak in a region of interest. In response to a detecting the presence of the contrast agent peak, centrally phase encoded data lines are generated.

One advantage of the present invention is that it captures the time-variant infusion effect of the bolus traveling in blood vessels so that it adaptively matches the phase encoding steps during data collection without extra time penalties, such as using navigator echoes.

Another advantage is that it does not depend on a guess or empirical assumption of the bolus arrival characteristics, nor does it depend on the accuracy of the bolus detection time point.

Another advantage of the present invention is the efficient collection of data since it does not depend on undersampling and consequent loss of high and middle frequency information.

Another advantage of the present invention is that it allows the tracking and prediction of bolus concentration changes.

Another advantage of the present invention is that it avoids artifacts related to the dynamic changes of subjects, such as signal clipping and others.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 1A illustrates an idealized timing window for acquisition of the central phase encoding and FIG. 1B illustrates the effect of early detection due to a discrepancy between assumed and actual bolus arrival characteristics.

DETAILED DESCRIPTION OF THE PREFERRED EMBODIMENTS

Figure 3:
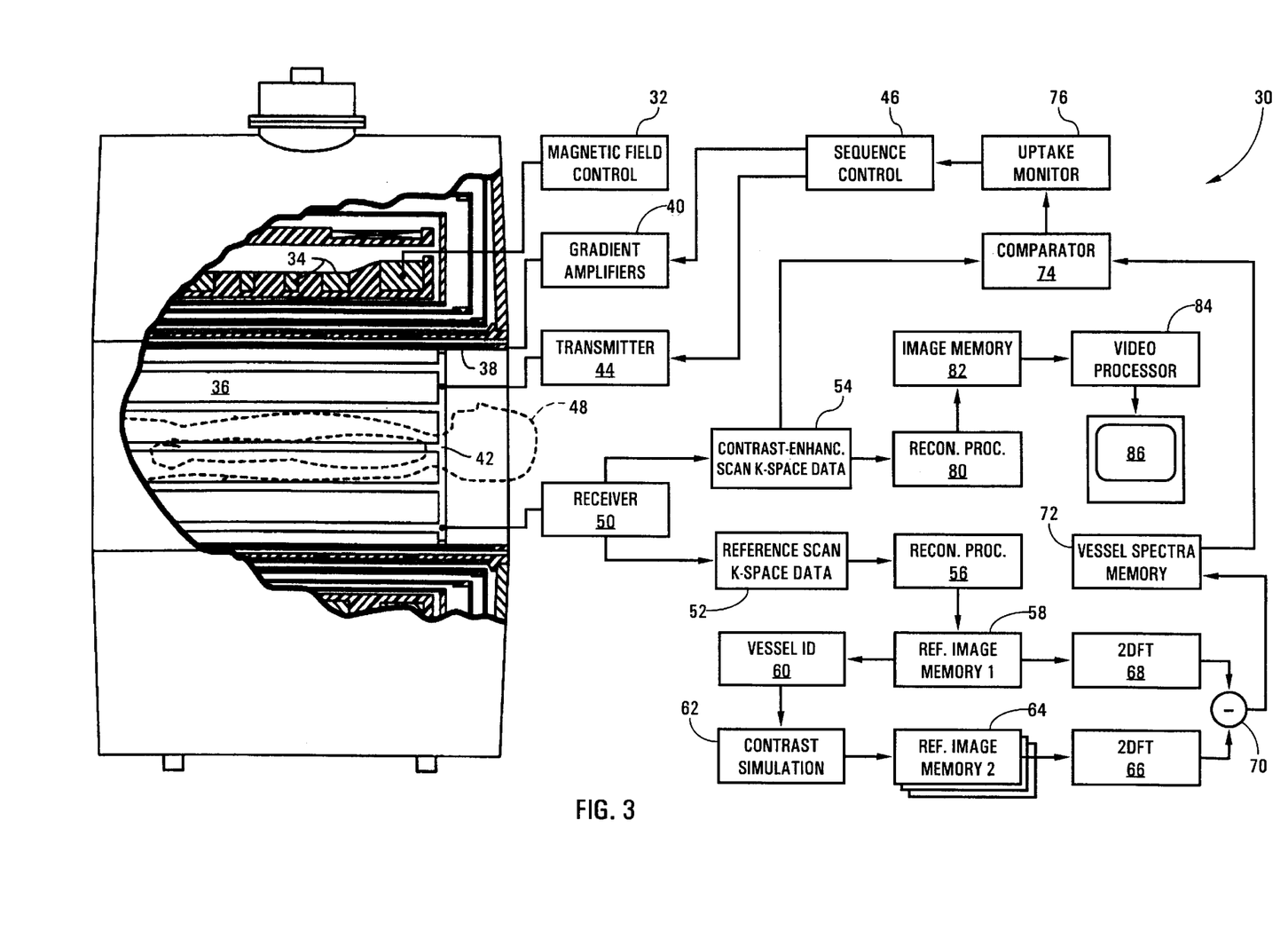
FIG. 3 is a diagrammatic illustration of a magnetic resonance imaging scanner including temporally resolved intensity tracing in accordance with aspects of the present invention.

With reference to FIG. 3, a magnetic resonance imaging system 30 includes a main magnetic field control 32 which controls superconducting, permanent, or resistive magnets 34 which create a substantially uniform, temporally constant magnetic field $B_0$ through an examination region 36. Although a bore-type magnet system is illustrated in FIG. 3, the present invention is equally applicable to other known types of MRI scanners, such as those using an open magnet system. A series of gradient coils 38 in conjunction with gradient amplifiers 40 generate magnetic field gradients across the examination region 36. Gradient amplifiers typically generate current pulses which result in corresponding gradient magnetic field pulses along the x-, y-, and z-axis for slab or slice selection, phase encoding, and read out or frequency encoding. Radio frequency coils 42 and a radio frequency transmitter 44 generate RF pulses that saturate, excite magnetic resonance, invert magnetization, refocus resonance, or manipulate magnetic resonance in selected portions of the examination region 36. A sequence control processor 46 controls the gradient pulse amplifiers 40 and the transmitter 44 to generate appropriate RF and gradient pulse sequences which may be any of a number of conventional scanning sequences, including, for example, two-dimensional techniques, three-dimensional techniques, dynamic methods, gated acquisitions, single or multi-echo acquisitions, and so forth. The sequence will generally be one of a plurality of user-selectable preprogrammed imaging sequences, e.g., stored in a sequence control memory of the sequence controller 46.

In certain embodiments, electrocardiographic gating is employed. An optional electrocardiograph (ECG) sensor (not shown) is attached to a subject 48 and outputs an electric ECG signal of the patient to an ECG gate pulse generator which, in turn, outputs a gate pulse as an ECG gating signal to the sequence controller 46. The gate pulses have a very small pulse width synchronous with the peak values of R-waves of the ECG signal. The gate pulses are utilized by the sequence controller 46 as an ECG gating signal to produce an ECG gated scan, e.g., by controlling the start timing and other sequence scanning parameters relative to the R-wave, as would be understood by those skilled in the art.

The radio frequency coil 42, or alternately, a surface coil array (not shown), is connected with a receiver 32 for demodulating the resultant resonance signals. The signals are amplified and demodulated by the receiver 32 and sampled into a k-space data memory. A first k-space data memory 52 receives reference scan data for the imaged region in the absence of a contrast agent and a second k-space data memory 54 receives contrast-enhanced data, i.e., acquired after a contrast agent is injected into the subject. The reference scan data is acquired prior to injection of the contrast agent. This prior information is then used to dynamically adjust the phase encoding in accordance with this teaching so as to acquire or, if necessary, reacquire, the central region of k-space when the contrast agent concentration reaches a plateau.

A first reconstruction processor 56 reconstructs the reference scan data 52 to form a first reference image representation stored in a first reference image memory 58. The first reference or baseline image may be any non-contrast enhanced magnetic resonance image of the region of interest which contains spatial information concerning the blood vessel or other region in which the drug or agent will be taken up. The first reference image is preferably an angiographic image, such as a maximum intensity projection image acquired with a time-of-flight or phase contrast technique. The reference image is preferably acquired immediately prior to the contrast-enhanced acquisition, and may be any precontrast image of a type which is typically taken before injection of the contrast agent, such as a mask image, an image used for position verification, and the like. The use of previously acquired and stored images is also contemplated.

A segmentation processor 60 isolates the vessel of interest, e.g., to generate a segmented image containing only spatial information of the vessel or otherwise identifying the pixels of the vessel. Image segmentation can be performed automatically under preprogrammed control, or can be performed manually by an operator, for example, by manipulating an on-screen pointing device while viewing the reference image on a display such as a display 86. A contrast simulation processor 62 artificially increases the intensity of the segmented pixels so as to approximate or estimate the intensity that would be expected if the contrast agent were present. The simulated intensities for the vessel can be based on intensities commonly found along the contrast agent uptake curve and/or an established theory. Of course, previously acquired timing information, if available, such as patient-specific or vessel-specific blood flow rate information, can also be used for generating the simulated intensities. The segmented region of the first reference image is then replaced with the simulated pixel intensities to generate a second reference image, which simulates the presence of the contrast agent, and which is stored in memory 64. Preferably two or more, and more preferably three or more, simulated reference images are generated using multiple time points along the contrast agent uptake curve to generate projected intensities at multiple times.

Figure 4:
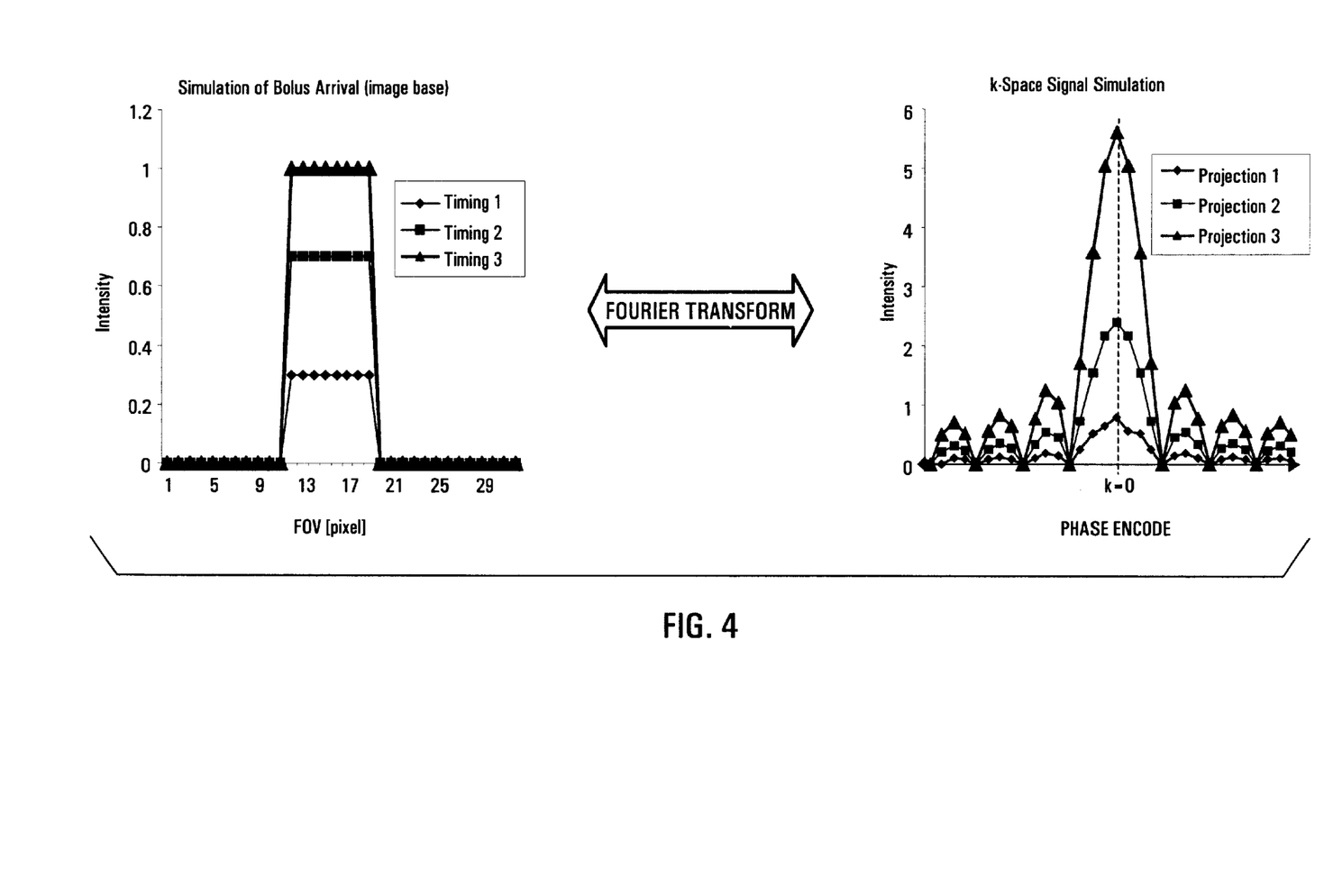
FIG. 4 illustrates a method of simulating contrast arrival kinetics by artificially increasing the pixel intensity of a selected spatial location in the image domain and transforming the results back into the frequency domain.

A first Fourier transform processor 66 performs a Fourier transform on each of the simulated reference images stored in memory 64 and a second Fourier transform processor 68 Fourier transforms the reference image stored in the memory 58 from the image domain to the frequency domain. Although two Fourier transform processors are shown for simplicity of illustration, it is to be appreciated that a single processor can be used. In Fourier space, the reference image 58 is subtracted from each of the simulated images with the numerically increased intensity by a subtraction processor 70 to generate spectra of the vessel with the contrast agent, which are stored in a memory 72. Since the spatially resolved information will not change during the process, the unique changes of the encoded time-domain signal is the intensity variation. That is to say, with given spatial information, i.e., the location of the blood vessel, the spectral pattern does not change except for the amplitude, which varies with the bolus arrival. In this manner, the frequency domain vessel spectra simulate the contrast agent uptake or arrival kinetics. An image domain plot of pixel intensity vs. pixel number for three time points along the contrast agent uptake curve and their corresponding frequency domain transforms are shown in FIG. 4. In this manner, projected k-space signal intensities can be projected for the points along the uptake curve.

Referring again to FIG. 3, after the projected vessel spectra are acquired, the patient is injected with a contrast agent and an imaging sequence is commenced by the sequence controller 46. The data acquisition can be commenced based on one of the prior art techniques for determining the beginning of contrast agent arrival or drug uptake. Data lines are collected into memory 54 using some preselected or conventional phase encoding strategy. A comparator or other processing logic 74 compares the collected k-space signal intensity with the various frequency spectra stored in the memory 72. A processor 76 derives bolus concentration information based on the frequency spectra or otherwise monitors the progress along the uptake curve. The contrast agent plateau is detected in one of two ways: (1) if, based on the comparison of the simulated spectra and the acquired k-space data, the intensity of the acquired signal matches the simulated spectrum indicative of the expected peak of the uptake curve; and (2) if the rate of change of the intensity of the spectrum indicates that the plateau has been reached. Upon detecting that the plateau has been reached, the sequence controller immediately adjusts the sequence to jump to and start collecting the central phase encode views. In an exemplary embodiment, if the peak signal is detected at pulse cycle TR(n), the phase encoding is adjusted so that zero phase encoding (k=0) is acquired within several pulse cycles, such as TR(n+1) or TR(n+2). After collection of the central phase encode views, the sequence returns to collect any remaining data lines. If, based on the original sequence, any central phase encode views are collected before the plateau is detected, the sequence controller dynamically adjusts the sequence to reacquire these views after the plateau period is detected. In this manner, the center plateau of the uptake curve is dynamically correlated with the central phase encode views.

In a preferred embodiment, a sequence is employed in which data lines with high and medium frequency phase encodings are collected first. The acquisition is then dynamically adjusted when the plateau period is detected to collect the central phase encode views, after which the sequence returns to collecting the high and mid frequency phase encode data lines.

A reconstruction processor 80, acting on the k-space data from the memory 54, implements a two-dimensional Fourier transform or other appropriate reconstruction algorithm generate an image representation stored in image memory 82. The reconstruction processor 80 may further include a projection algorithm such as a maximum intensity projection algorithm for generating a two-dimensional image representation from volume image data, e.g., acquired using a three-dimensional imaging technique or built up from multiple contiguous slices or slabs. The reconstruction processor 80 may optionally include additional modules providing functions appropriate to angiography, including processors or program modules for slice selection, angle selection, recrop, background suppression, interpolation, reconstruction grid repositioning, and the like. Although shown as two processors for conceptual simplicity, it is to be appreciated that processors 56 and 80 can share common hardware. The stored image representation is accessed by a video processor 84 that prepares or formats the image data for display on a human-viewable display 86.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of magnetic resonance imaging, comprising:
   acquiring a baseline magnetic resonance image of a region of interest in the absence of a contrast agent;
   simulating an increase in image intensity of a subregion of interest within the region of interest, the subregion being subject to increased image intensity in the presence of a contrast agent;
   correlating magnetic resonance k-space signal intensity with contrast agent concentration in the subregion;
   administering a contrast agent to the subject;
   acquiring k-space data for the region of interest;
   monitoring the k-space data signal intensity to derive contrast agent concentration information;
   detecting a peak contrast agent concentration from the monitored k-space data signal intensity;
   after the peak contrast agent concentration is detected, immediately adjusting the phase encoding so that k-space data with zero phase encoding is acquired.

2. The method of claim 1, wherein the subregion is a blood vessel and further wherein the contrast agent is injected into the subject.

3. The method of claim 1, further including:
   converting the k-space data into an image representation.

4. The method of claim 2, wherein the step of correlating magnetic resonance k-space signal intensity with contrast agent concentration includes:
   segmenting the blood vessel;
   simulating intensity changes for the vessel due to the presence of a contrast agent at a plurality of concentrations;
   computing a simulated frequency domain spectrum for the vessel for each of the plurality of concentrations.

5. The method of claim 4, wherein the frequency domain spectra are calculated by:
   generating images having artificially increased pixel intensities at spatial locations corresponding to the vessel;
   Fourier transforming each of the baseline image and said generated images from the image domain to the frequency domain; and
   in the frequency domain, subtracting the baseline image from each of said generated images.

6. The method of claim 5, wherein the step of monitoring the k-space signal intensity includes one or both of:
   comparing the acquired k-space data with the simulated frequency domain spectra; and
   comparing the acquired k-space data with previously acquired k-space data to detect a change in the rate of change of k-space signal intensity as a function of time.

7. The method of claim 2, wherein the baseline image representation is generated with one of a time-of-flight magnetic resonance angiographic technique and a phase contrast magnetic resonance angiographic technique.

8. The method of claim 1, further including:
   during the acquisition of the k-space data from the region of interest, controlling acquisition of data from the volume of interest in accordance with a monitored physiological movement.

9. The method of claim 2, further including:
   during the acquisition of the k-space data from the region of interest, controlling acquisition of data from the volume of interest in accordance with a cardiac cycle.

10. The method of claim 1, wherein the baseline images are segmented automatically.

11. The method of claim 1, wherein the baseline images are segmented manually.

12. The method of claim 1, wherein the step of acquiring k-space data includes:
    acquiring k-space data with middle or low frequency phase encoding, including zero phase encoding, before the peak contrast agent concentration is detected; and
    replacing the k-space data with zero phase encoding acquired before the peak contrast agent concentration is detected with said k-space data with zero phase encoding acquired after the peak contrast agent concentration is detected.

13. The method of claim 1, wherein the step of acquiring k-space data includes:

acquiring only data views selected from one or both of high frequency data lines and middle frequency data lines before the peak contrast agent concentration is detected.

14. A magnetic resonance imaging system having means for generating a magnetic field in an examination region, a radio frequency pulse controller and transmitter for inducing dipoles in the examination region to resonance such that radio frequency resonance signals are generated, gradient magnetic field coils and a gradient magnetic field controller for performing a pulse sequence including at least phase and read magnetic field gradient pulses in orthogonal directions across the examination region, a receiver for receiving and demodulating the radio frequency magnetic resonance signals, and an image processing system for reconstructing image representations, the image processing system including:

a memory for storing a baseline image representation of a region of interest in the absence of a contrast agent;

a first processor for identifying the spatial location of a subregion of interest within the region of interest, the subregion of interest being subject to increased image intensity in the presence of a contrast agent and for generating and storing simulated image representations of the region of interest in which the subregion is artificially increased;

a second image processor that calculates and stores frequency domain spectra for the subregion of interest based on differences between the baseline image and the simulated images;

a third processor that detects peak contrast agent concentration in the region of interest by monitoring k-space signal intensity received after a contrast agent is administered to a subject to be imaged;

the gradient magnetic field controller responds to detection of the peak contrast agent composition by dynamically adjusting the pulse sequence to collect k-space data lines with central phase encoding; and a reconstruction processor that generates image representations from the magnetic resonance signals.

15. The imaging system of claim 14, wherein the peak contrast agent concentration is detected by one or both of:

comparing a received k-space signal intensity with said frequency domain spectra; and monitoring a rate of change in received k-space signal intensity.

16. The imaging system of claim 14, further including:

a display apparatus that converts the image representations into a human-viewable images.

17. The imaging system according to claim 14, further comprising an electrocardiographic sensor.

18. The imaging system of claim 14, wherein the third image processor calculates the frequency domain spectra by:

Fourier transforming each of the baseline image representation and the simulated image representations from the image domain to the frequency domain; and in the frequency domain, subtracting the baseline image from each of the simulated images.

19. The imaging system of claim 14, wherein the baseline image representation is generated with one of a time-of-flight magnetic resonance angiographic technique and a phase contrast magnetic resonance angiographic technique.

20. The imaging system of claim 14, further including:

the gradient magnetic field controller generates only data views selected from high and middle frequency data lines prior to detection of the peak contrast agent composition.

21. The imaging system of claim 14, further including:

the gradient magnetic field controller generates only data views selected from one or both of middle frequency data lines or low frequency data lines prior to detection of the peak contrast agent composition.

22. A method of magnetic resonance imaging comprising:

generating a plurality of data lines having high and middle frequency phase encoding;

comparing a frequency spectrum of each data line with a reference frequency spectrum indicative of a presence of contrast agent peak in a region of interest; and in response to the comparing determining the presence of the contrast agent peak, generating centrally phase-encoded data lines.

23. The method of claim 22, further including generating the reference frequency spectrum by:

generating an image including the region of interest;

numerically simulating the presence of the contrast agent peak in at least one subregion of the region of interest; and determining a frequency spectrum difference between the generated image and the image with the numerically simulated contrast agent peak.

24. The method of claim 23, wherein the determining step includes:

transforming at least corresponding portions of the generated image and the image with the numerically simulated contrast agent peak into frequency space; and comparing the frequency spectra of the two images in frequency space.

* * * * *